United States Patent
Flohr et al.

(10) Patent No.: US 9,730,811 B2
(45) Date of Patent: Aug. 15, 2017

(54) DEVICE FOR TESTING A CERAMIC SOCKET INSERT FOR HIP JOINT IMPLANTS

(71) Applicant: CeramTec GmbH, Plochingen (DE)

(72) Inventors: Markus Flohr, Esslingen (DE); Hendrik Bertmaring, Esslingen (DE); Kim Lars Häussler, Esslingen (DE); Helena Graf, Stuttgart (DE)

(73) Assignee: CERAMTEC GmbH, Plochingen (DE)

( * ) Notice: Subject to any disclaimer, the term of this patent is extended or adjusted under 35 U.S.C. 154(b) by 278 days.

(21) Appl. No.: 14/383,330

(22) PCT Filed: Mar. 6, 2013

(86) PCT No.: PCT/EP2013/054469
§ 371 (c)(1),
(2) Date: Sep. 5, 2014

(87) PCT Pub. No.: WO2013/131938
PCT Pub. Date: Sep. 12, 2013

(65) Prior Publication Data
US 2015/0020602 A1  Jan. 22, 2015

(30) Foreign Application Priority Data
Mar. 6, 2012 (DE) .................. 10 2012 203 513

(51) Int. Cl.
*G01N 3/02* (2006.01)
*A61F 2/46* (2006.01)
(Continued)

(52) U.S. Cl.
CPC ............. *A61F 2/468* (2013.01); *G01N 3/02* (2013.01); *A61F 2/34* (2013.01);
(Continued)

(58) Field of Classification Search
CPC .. A61F 2/468; A61F 2/34; A61F 2002/30332; A61F 2002/30345;
(Continued)

(56) References Cited

U.S. PATENT DOCUMENTS 4,126,924 A * 11/1978 Akins ................. A61F 2/30767
29/423
4,645,508 A * 2/1987 Shorter ................. A61F 2/6607
623/48
(Continued)

FOREIGN PATENT DOCUMENTS

| DE | 2418956 B1 | 4/1975 |
| DE | 198 41 826 A1 | 3/2000 |
| EP | 0 921 771 B1 | 10/2002 |

*Primary Examiner* — Jonathan Dunlap
(74) *Attorney, Agent, or Firm* — Norton Rose Fulbright US LLP; James Crawford

(57) ABSTRACT

The invention relates to a device for testing a ceramic socket insert for hip joint implants having a receiving device, a pressure piece and optionally having a plunger, wherein the receiving device has a recess with a positioning region for receiving the socket insert and the recess has a receiving cone in the positioning region. According to the invention, in order for the device to be universally applicable to all socket inserts (monolithic, modular, pre-joined) and therefore replace all current devices, an annular ductile adapter piece having a conical outer surface contacting the receiving cone and an inner surface contacting the socket insert is arranged in the positioning region between the receiving device and the socket insert, wherein the friction between the receiving device and adapter piece is lower than between the adapter piece and socket insert.

16 Claims, 1 Drawing Sheet

(51) Int. Cl.
 *G01N 3/08* (2006.01)
 *A61F 2/30* (2006.01)
 *A61F 2/34* (2006.01)

(52) U.S. Cl.
 CPC ............ *A61F 2002/30332* (2013.01); *A61F 2002/30345* (2013.01); *A61F 2002/30649* (2013.01); *A61F 2002/4666* (2013.01); *A61F 2310/00077* (2013.01); *A61F 2310/00179* (2013.01); *G01N 3/08* (2013.01); *G01N 2203/0276* (2013.01); *G01N 2203/0452* (2013.01)

(58) Field of Classification Search
 CPC .... A61F 2002/4666; A61F 2002/30649; A61F 2310/00077; A61F 2310/00179; G01N 3/02; G01N 3/08; G01N 2203/0276; G01N 2203/0452
 USPC ........... 623/23.11, 11.11, 22.18, 22.19, 22.2, 623/23.4; 73/818, 788, 790, 821, 831, 73/856, 864.91
 See application file for complete search history.

(56) References Cited

U.S. PATENT DOCUMENTS

| | | | | |
|---|---|---|---|---|
| 5,549,693 | A | * | 8/1996 | Roux .................... A61L 27/105 623/22.14 |
| 5,676,701 | A | * | 10/1997 | Yuan ..................... A61L 27/045 606/247 |
| 6,176,140 | B1 | | 1/2001 | Autenrieth et al. |
| 6,564,647 | B1 | | 5/2003 | Richter et al. |
| 6,901,811 | B2 | * | 6/2005 | Babler ................... A61F 2/468 73/824 |
| 7,493,828 | B2 | * | 2/2009 | Greenwald ............. A61F 2/468 73/818 |
| 2003/0077110 | A1 | * | 4/2003 | Knowles ................ F16L 27/04 403/56 |
| 2005/0033445 | A1 | * | 2/2005 | Siebel ................ A61B 17/1666 623/22.15 |
| 2008/0233838 | A1 | * | 9/2008 | Mase ....................... B24C 1/06 451/38 |

* cited by examiner

DEVICE FOR TESTING A CERAMIC SOCKET INSERT FOR HIP JOINT IMPLANTS

This application is a §371 of International Application No. PCT/EP2013/054469 filed Mar. 6, 2013, and claims priority from German Patent Application No. 10 2012 203 513.3 filed Mar. 6, 2012.

FIELD OF THE INVENTION

The invention relates to a device for testing a ceramic socket insert for hip joint implants with a holding fixture, a pressure piece and optionally a plunger.

BACKGROUND OF THE INVENTION

A large number of prosthesis-systems exist on the market for replacement of the natural hip joint. These are made, as shown in FIG. 1, as a rule from a shaft 1 coupled with a ball head 2 and a synthetic acetabular cup 4 coupled with a socket insert 3. Shaft 1 and acetabular cup 4 are attached to the body mostly through ingrowth in the femur and/or hip bones and are carriers for ball head 2 and/or socket insert 3. The ball head 2 is rotatably mounted in the calotte of the socket insert 3 and forms a wear couple with this. Various materials such as ceramics, among others, are used for the gliding partner. Modular systems as described above exist on the acetabular side of the wear couple, which means that acetabular cups and socket inserts are supplied separately and accordingly are only joined in situ. In addition, monolithic systems exist which have only a single acetabular component and are inserted directly into the hip bones, and preassembled systems in which acetabular cup and socket insert are already joined together by the manufacturer.

The required minimum strength of ceramic acetabular hip joint implants is frequently ensured by a proof test (100%-checkup). Thereby the acetabular hip joint implant is mechanically stressed. This is described in EP 0 921 771 A1 or DE 198 41 826. 100%-check means that the equipment is mechanically stressed before delivery and components with critical defects break in the proof test, so that only components having sufficiently high mechanical strength pass the proof test.

At present, various test setups are in use for the many specific geometries of the acetabular hip joint implants. This requires a multitude of test setups and also a large storage capacity.

OBJECTS AND SUMMARY OF THE INVENTION

The object of the invention is to improve a device for testing a ceramic socket insert for hip joint implants in such a way that the device can be used universally for all acetabular hip joint implants (monolithic, modular, preassembled) thus replacing all current devices.

This object is achieved according to the invention by means of the features of the present invention.

DETAILED DESCRIPTION

Figure 1:
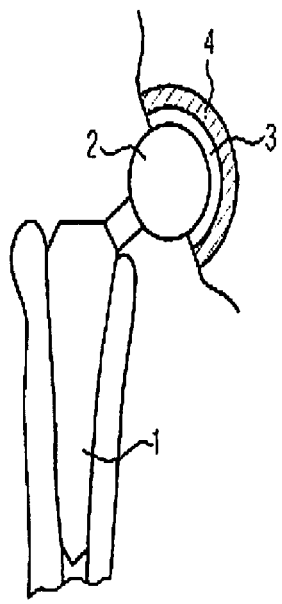
FIG. 1 depicts a prosthesis-system for the replacement of the natural hip joint.

Thereby, in the positioning region between the holding fixture and the socket insert there is disposed an annular ductile adaptor piece with a conical outer surface, which abuts the receiving cone and an inner surface which abuts the socket insert, wherein the friction between the holding fixture and the adaptor piece is less than between the adaptor piece and the socket insert, under load a relative movement is produced mainly between holding fixture and adaptor piece. This ensures, in combination with the conically structured holding fixture and/or the receiving cone, an increase of the radially-acting force components. Thereby the device according to the invention can be used universally for all acetabular hip joint implants (monolithic, modular, preassembled).

Due to a targeted constant diffusion of stress on the outer contour of the socket insert, nearly all load situations, which the socket insert and/or the implant can experience under in vivo conditions, are covered.

Preferably the receiving cone is polished at least in the positioning area. Thereby the adaptor piece glides more easily on the receiving cone and/or the holding fixture.

In one embodiment of the invention the adaptor piece is made from metal and the holding fixture from surface-hardened steel.

Preferably between the conical outer surface of the adaptor piece and the receiving cone and/or between the inner surface of the adaptor piece and the socket insert an angular gap x° is disposed, wherein the angular gap x° starting from the top, enlarges downward to the end of the receiving cone facing the socket insert.

In this way it is ensured that the receiving surface and/or contact surface, under increasing load between holding fixture and adaptor piece and/or between adaptor piece and socket insert, forms starting from the front side of the socket insert. The angular gap x° or angular gaps ensure that the socket insert is stressed in accordance with the later in vivo use. In addition, tensile stresses are already provided in the cone area.

The angular gap ensures, that the tensile stresses from the front side, form/continue out via the cone area in rear side direction. This may vary for different components. Preferably the angular gap x° is between 30 angular seconds and 20 angular minutes. Between 6 and 10 angular minutes is especially preferred. In one embodiment, in particular 8 angular minutes proved to be advantageous. With increasing stress this angular gap should be bypassed and is therefore limited upward. The tolerance range depends on circumstances of the stress level.

In one embodiment using a stamp for the force application of the pressure piece, the material of the stamp is harder than the material of the pressure piece, wherein the stamp is preferably made from hardened steel and the pressure piece from a plastic. Teflon is eminently suitable.

The socket insert, also referred to as implant, is thus positioned during the proof test via a holding fixture and then is stressed. An adaptor piece made from ductile material is disposed between implant and holding fixture. Thereby it is ensured that the adaptor piece can adjust itself to the implant. Ideally the adaptor piece consists of brass and the holding fixture consists of hardened steel. The area of the holding fixture in which the adaptor piece and the implant are positioned is conical in shape. Thereby applied forces are broken down into their normal and radially acting components. The material of the holding fixture is arranged in the positioning area in such a way that the friction between the holding fixture and adaptor piece is less than between adaptor piece and implant. In the ideal case, this area should be polished. Thereby under load a relative movement mainly between holding fixture and adaptor is provided. This guarantees in combination with the conically shaped holding fixture a heightening of the radially acting force components.

The actual load introduction can take place via the front face or calotte of the implant, or also via the adaptor piece. Ideally, however, the load can be introduced via a plunger and a pressure piece fastened thereon, which is adjusted to the inner contour of the implant. The material of the pressure piece adapted to the plunger should be sufficiently ductile to ensure adjustment under load to the exact inner contour of the implant. Ideally the pressure piece consists of Teflon. The plunger must be harder than the pressure piece and should preferably consist of hardened steel. Thus the best possible constant course of tension is provided on the outer contour.

FIG. 1 depicts a known hip joint implant as described in the description preamble.

Figure 2:
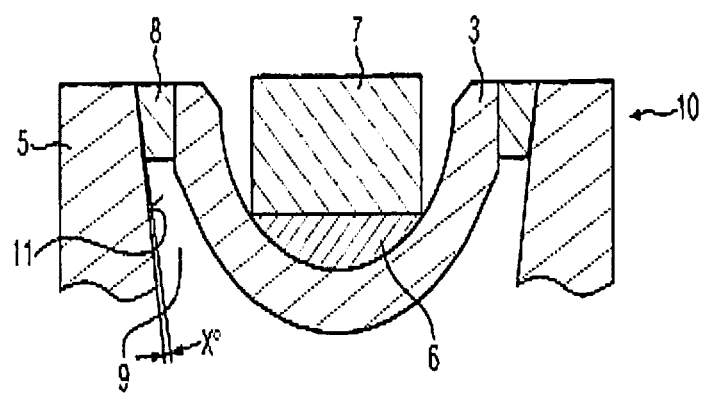
FIG. 2 depicts a device according to the invention for testing a ceramic socket insert 3 of a hip joint implant.

FIG. 2 depicts a device according to the invention for testing a ceramic socket insert 3 of a hip joint implant. The device consists of a holding fixture 5, a pressure piece 6 and a plunger 7, wherein a recess 9 having a positioning region 10 for uptake of the socket insert (3) is disposed in the holding fixture 5 and the recess 9 has a receiving cone 11 in the positioning region 10.

An annular, ductile, brass adapter piece 8 with a conical outer surface, which abuts the receiving cone 11 and an inner surface which abuts the socket insert, is arranged in the positioning region 10 between the holding fixture 5 and the socket insert 3.

In an alternative embodiment, not shown here, the angular gap can also or only be set up between the inner surface of the adapter piece and the socket insert.

For the testing of a socket insert 3, this is inserted into the holding fixture 5 via an annular adaptor piece 8. Subsequently, the pressure piece 6 is loaded via the plunger 7. If the socket insert 3 breaks, it was defective. If it does not break, then it is certain that it will not break under forces beneath the applied testing force.

A critical feature of the device is that the friction between the holding fixture and adaptor piece is less than between adaptor piece and implant. Thereby under load a relative movement mainly between holding fixture and adaptor is provided. In this way, a best possible constant course of tension on the outer contour of the socket insert is provided, so that this device can be used for all socket inserts.

It is claimed:

1. A device for testing a ceramic socket insert of hip joint implants comprising:
   a holding fixture; and
   a pressure piece;
   wherein the holding fixture comprises a recess having a positioning region for uptake of the socket insert; and
   wherein the recess in the positioning region has a receiving cone;
   wherein in the positioning region between the holding fixture and the socket insert there is disposed an annular, ductile adaptor piece with a conical outer surface, which abuts the receiving cone and an inner surface which abuts the socket insert,
   wherein the receiving cone of the holding fixture is polished at least in the positioning area so that the adaptor piece glides more easily on at least one of the receiving cone and the holding fixture.

2. A device according to claim 1, wherein the holding fixture consists of surface-hardened steel.

3. A device according to claim 2, wherein the adaptor piece is made of brass.

4. A device according to claim 2, wherein the adaptor piece has a conical outer surface and an inner surface, and wherein between the conical outer surface of the adaptor piece and the receiving cone of the recess and/or between the inner surface of the adaptor piece and the socket insert an angular gap x° is provided, wherein the angular gap x° starting from the top, enlarges downward to an end of the receiving cone facing the socket insert, wherein the angular gap x° is between 30 angular seconds and 20 angular minutes.

5. A device according to claim 1, wherein the adaptor piece is made of brass.

6. A device according to claim 5, wherein the holding fixture consists of surface-hardened steel.

7. A device according to claim 6, wherein the adaptor piece has a conical outer surface and an inner surface, and wherein between the conical outer surface of the adaptor piece and the receiving cone of the recess and/or between the inner surface of the adaptor piece and the socket insert an angular gap x° is provided, wherein the angular gap x° starting from the top, enlarges downward to an end of the receiving cone facing the socket insert, wherein the angular gap x° is between 30 angular seconds and 20 angular minutes.

8. A device according to claim 5, wherein the adaptor piece has a conical outer surface and an inner surface, and wherein between the conical outer surface of the adaptor piece and the receiving cone of the recess and/or between the inner surface of the adaptor piece and the socket insert an angular gap x° is provided, wherein the angular gap x° starting from the top, enlarges downward to an end of the receiving cone facing the socket insert, wherein the angular gap x° is between 30 angular seconds and 20 angular minutes.

9. A device according to claim 1, wherein the adaptor piece has a conical outer surface and an inner surface, and wherein between the conical outer surface of the adaptor piece and the receiving cone of the recess and/or between the inner surface of the adaptor piece and the socket insert an angular gap x° is provided, wherein the angular gap x° starting from the top, enlarges downward to an end of the receiving cone facing the socket insert, wherein the angular gap x° is between 30 angular seconds and 20 angular minutes.

10. A device according to claim 9, wherein the angular gap x° is between 6 and 10 angular minutes.

11. A device according to claim 10, wherein the angular gap x° is 8 angular minutes.

12. A device according to claim 9, wherein the holding fixture consists of surface-hardened steel.

13. A device according to claim 1, further comprising a plunger for applying the force of the pressure piece, wherein the material of the plunger is harder than the material of the pressure piece, wherein the plunger comprises hardened steel and the pressure piece is plastic.

14. A device according to claim 13, wherein the plastic is Teflon.

15. A device according to claim 1, further comprising a plunger.

16. A device according to claim 15, wherein the holding fixture consists of surface-hardened steel.

* * * * *